(12) United States Patent
Ariyama et al.

(10) Patent No.: US 12,685,483 B2
(45) Date of Patent: Jul. 21, 2026

(54) PHYSIOLOGICAL INFORMATION PROCESSING DEVICE, PHYSIOLOGICAL INFORMATION PROCESSING METHOD, AND STORAGE MEDIUM

(71) Applicants:Nihon Kohden Corporation, Tokyo (JP); Hiroshima Prefecture, Hiroshima (JP)

(72) Inventors: Tetsuri Ariyama, Tokorozawa (JP); Minoru Matsushima, Tokorozawa (JP); Hideki Ochiai, Tokorozawa (JP); Nobuyuki Yasumaru, Tokorozawa (JP); Rie Fukuhara, Hiroshima (JP)

(73) Assignees: Nihon Kohden Corporation, Tokyo (JP); Hiroshima Prefecture, Hiroshima (JP)

( * ) Notice: Subject to any disclaimer, the term of this patent is extended or adjusted under 35 U.S.C. 154(b) by 278 days.

(21) Appl. No.: 18/337,801

(22) Filed: Jun. 20, 2023

(65) Prior Publication Data

US 2023/0414168 A1       Dec. 28, 2023

(30) Foreign Application Priority Data

Jun. 27, 2022    (JP) ................................. 2022-102808

(51) Int. Cl.
*A61B 5/00*          (2006.01)
*A61B 5/0205*      (2006.01)
(Continued)

(52) U.S. Cl.
CPC .......... *A61B 5/4824* (2013.01); *A61B 5/0205* (2013.01); *A61B 5/14542* (2013.01);
(Continued)

(58) Field of Classification Search
CPC . A61B 5/4824; A61B 5/0205; A61B 5/14542; A61B 5/748; A61B 5/024;
(Continued)

(56) References Cited

U.S. PATENT DOCUMENTS 9,326,725 B2     5/2016   Finkel et al.
11,202,604 B2 *   12/2021   Alzamzmi ........... G06V 40/176
(Continued)

FOREIGN PATENT DOCUMENTS

CN          112741593  A      5/2021
JP            6605422  B2    10/2019

OTHER PUBLICATIONS

Office Action issued in Japanese Patent Application No. 2022-102808, mailed on Feb. 3, 2026, 7 pages including 4 pages of machine English translation.

(Continued)

*Primary Examiner* — Michael J Lau
(74) *Attorney, Agent, or Firm* — Dorsey & Whitney LLP

(57)          ABSTRACT

A physiological information processing device includes one or more processors, and one or more memories for storing computer-readable commands. When the computer-readable commands are executed by the processors, the physiological information processing device executes processing of acquiring attribute information associated with an attribution of an infant, acquiring state information related to a state of the infant before a start of a pain event that causes pain in the infant, acquiring physiological information data of the infant, acquiring facial expression information associated with infant's facial expression after the start of the pain event, calculating a pain assessment index for assessing the pain of the infant in the pain event based on the attribute information, the state information, the physiological infor-
(Continued)

mation data, and the facial expression information, and outputting the calculated pain assessment index.

15 Claims, 9 Drawing Sheets

(51) Int. Cl.
| | |
|---|---|
| *A61B 5/145* | (2006.01) |
| *G16H 50/30* | (2018.01) |
| *A61B 5/024* | (2006.01) |

(52) U.S. Cl.
CPC ............. *A61B 5/748* (2013.01); *G16H 50/30* (2018.01); *A61B 5/024* (2013.01); *A61B 2503/04* (2013.01)

(58) Field of Classification Search
CPC .......... A61B 2503/04; A61B 2503/045; A61B 5/163; A61B 5/165; A61B 5/7275; G16H 50/30; G16H 40/63; G16H 50/20
See application file for complete search history.

(56) References Cited

U.S. PATENT DOCUMENTS

| | | | | |
|---|---|---|---|---|
| 11,631,280 | B2 * | 4/2023 | Mouton ............... | A61B 5/4824 382/128 |
| 11,992,331 | B2 * | 5/2024 | Alzamzmi ........... | A61B 5/7267 |

| | | | | |
|---|---|---|---|---|
| 2017/0156661 | A1 * | 6/2017 | Hughes ................ | A61B 5/0013 |
| 2019/0320974 | A1 | 10/2019 | Alzamzmi et al. | |
| 2019/0371028 | A1 * | 12/2019 | Harrises ............. | G02B 27/0101 |
| 2021/0052215 | A1 | 2/2021 | Mouton et al. | |
| 2023/0309915 | A1 * | 10/2023 | Salekin ................ | A61B 5/0077 600/301 |
| 2023/0414168 | A1 * | 12/2023 | Ariyama ................ | G16H 50/30 |

OTHER PUBLICATIONS

Office Action issued in Japanese Patent Application No. 2022-102808, mailed on May 11, 2026, 12 pages including 7 pages of machine English translation.

Kaur, et al., "Study of Pain Response in Neonates During Venipuncture with a View to Analyse Utility of Topical Anaesthetic Agent for Alleviating Pain", Medical Journal Armed Forces India, vol. 75, No. 2, pp. 140-145, Feb. 4, 2018, Elsevier.

Madathil, et al., "NOPAIN-ROP Trial: Intravenous Fentanyl and Intravenous Ketamine for Pain Relief During Laser Photocoagulation for Retinopathy of Prematurity (ROP) in Preterm Infants: A Randomised Trial", BMJ Open, vol. 11, e046235, 9 pages, Sep. 16, 2021.

Madathil, et al., "NOPAIN-ROP Trial: Intravenous Fentanyl and Intravenous Ketamine for Pain Relief During Laser Photocoagulation for Retinopathy of Prematurity (ROP) in Preterm Infants: A Randomised Trial; Supplemental Material", BMJ Open, vol. 11, e046235, 147 pages, Sep. 16, 2021.

* cited by examiner

*FIG. 5*

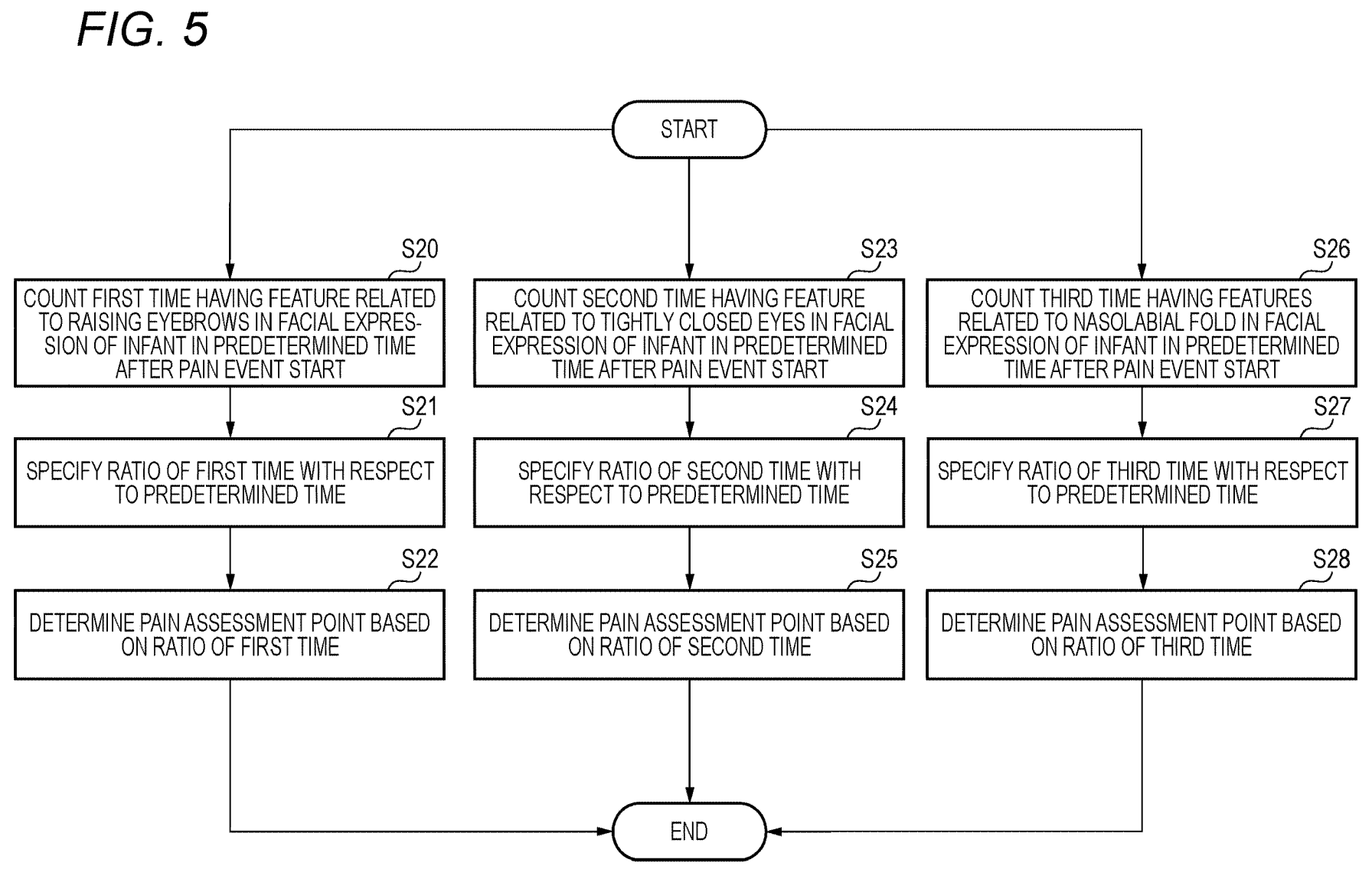

START

S20 COUNT FIRST TIME HAVING FEATURE RELATED TO RAISING EYEBROWS IN FACIAL EXPRESSION OF INFANT IN PREDETERMINED TIME AFTER PAIN EVENT START

S21 SPECIFY RATIO OF FIRST TIME WITH RESPECT TO PREDETERMINED TIME

S22 DETERMINE PAIN ASSESSMENT POINT BASED ON RATIO OF FIRST TIME

S23 COUNT SECOND TIME HAVING FEATURE RELATED TO TIGHTLY CLOSED EYES IN FACIAL EXPRESSION OF INFANT IN PREDETERMINED TIME AFTER PAIN EVENT START

S24 SPECIFY RATIO OF SECOND TIME WITH RESPECT TO PREDETERMINED TIME

S25 DETERMINE PAIN ASSESSMENT POINT BASED ON RATIO OF SECOND TIME

S26 COUNT THIRD TIME HAVING FEATURES RELATED TO NASOLABIAL FOLD IN FACIAL EXPRESSION OF INFANT IN PREDETERMINED TIME AFTER PAIN EVENT START

S27 SPECIFY RATIO OF THIRD TIME WITH RESPECT TO PREDETERMINED TIME

S28 DETERMINE PAIN ASSESSMENT POINT BASED ON RATIO OF THIRD TIME

END

*FIG. 7*

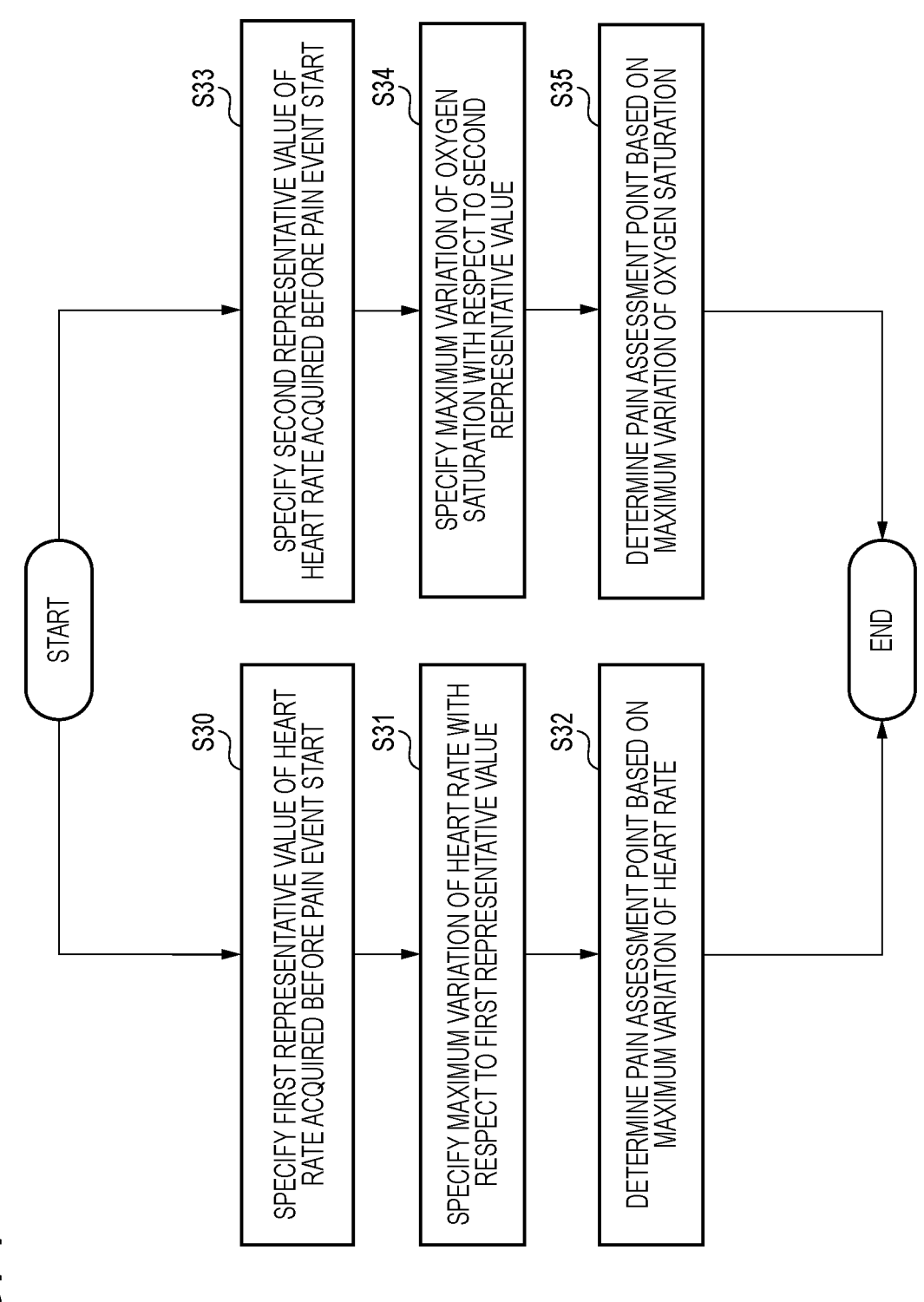

START

S30
SPECIFY FIRST REPRESENTATIVE VALUE OF HEART RATE ACQUIRED BEFORE PAIN EVENT START

S31
SPECIFY MAXIMUM VARIATION OF HEART RATE WITH RESPECT TO FIRST REPRESENTATIVE VALUE

S32
DETERMINE PAIN ASSESSMENT POINT BASED ON MAXIMUM VARIATION OF HEART RATE

S33
SPECIFY SECOND REPRESENTATIVE VALUE OF HEART RATE ACQUIRED BEFORE PAIN EVENT START

S34
SPECIFY MAXIMUM VARIATION OF OXYGEN SATURATION WITH RESPECT TO SECOND REPRESENTATIVE VALUE

S35
DETERMINE PAIN ASSESSMENT POINT BASED ON MAXIMUM VARIATION OF OXYGEN SATURATION

END

*FIG. 8*

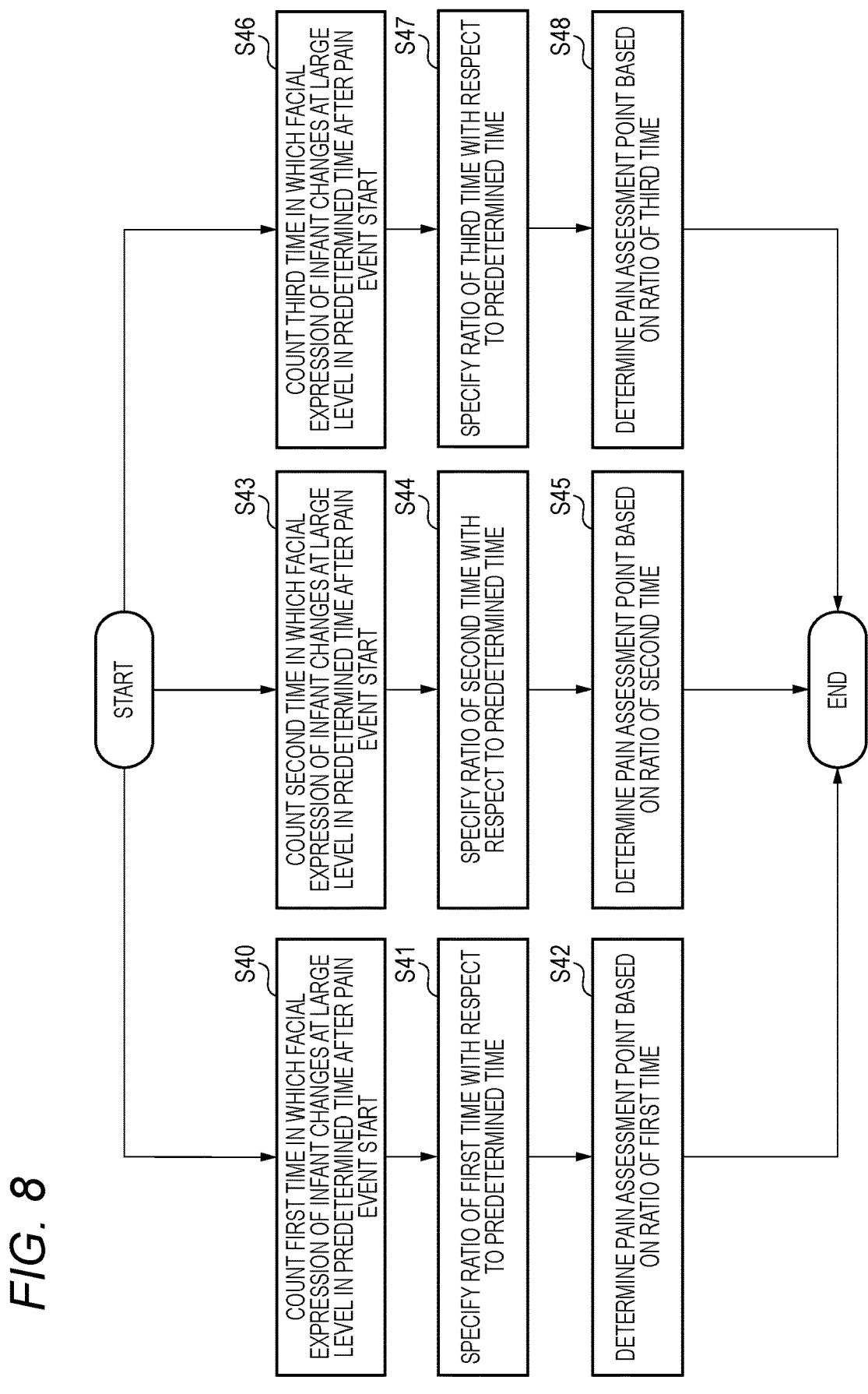

START

S40 COUNT FIRST TIME IN WHICH FACIAL EXPRESSION OF INFANT CHANGES AT LARGE LEVEL IN PREDETERMINED TIME AFTER PAIN EVENT START

S41 SPECIFY RATIO OF FIRST TIME WITH RESPECT TO PREDETERMINED TIME

S42 DETERMINE PAIN ASSESSMENT POINT BASED ON RATIO OF FIRST TIME

S43 COUNT SECOND TIME IN WHICH FACIAL EXPRESSION OF INFANT CHANGES AT LARGE LEVEL IN PREDETERMINED TIME AFTER PAIN EVENT START

S44 SPECIFY RATIO OF SECOND TIME WITH RESPECT TO PREDETERMINED TIME

S45 DETERMINE PAIN ASSESSMENT POINT BASED ON RATIO OF SECOND TIME

S46 COUNT THIRD TIME IN WHICH FACIAL EXPRESSION OF INFANT CHANGES AT LARGE LEVEL IN PREDETERMINED TIME AFTER PAIN EVENT START

S47 SPECIFY RATIO OF THIRD TIME WITH RESPECT TO PREDETERMINED TIME

S48 DETERMINE PAIN ASSESSMENT POINT BASED ON RATIO OF THIRD TIME

END

PHYSIOLOGICAL INFORMATION PROCESSING DEVICE, PHYSIOLOGICAL INFORMATION PROCESSING METHOD, AND STORAGE MEDIUM

CROSS-REFERENCE TO RELATED APPLICATIONS

This application is based upon and claims the benefit of priority from Japanese Patent Application No. 2022-102808, filed Jun. 27, 2022, the entire contents of which are incorporated herein by reference.

TECHNICAL FIELD

The present disclosure relates to a physiological information processing device and a physiological information processing method. The present disclosure relates to a program for causing a computer to execute the physiological information processing method, and a computer readable storage medium in which the program is stored.

BACKGROUND ART

Most premature infants and immature infants (hereafter, premature infants and the like) will be treated and examined in the neonatal intensive care unit (NICU), and treatment and examination for premature infants and the like may require procedures accompanying pain. It is said that the experience of pain in the neonatal period may adversely affect the sensitivity to pain and the stress system of the autonomic nervous system. On the other hand, newborns cannot express pain from themselves because they cannot communicate. Thus, in pain events such as blood collection, means for enabling healthcare professionals to accurately grasp neonatal pain is desired.

Therefore, JP6605422B discloses a pain assessment system that assesses infant pain from an infant's electroencephalogram signal by applying electrical stimulation to the infant.

SUMMARY OF INVENTION

Incidentally, in the pain assessment system disclosed in JP6605422B, when the infant's body moves frequently, since the electromyographic signal is superimposed on the electroencephalogram signal, there is a possibility that it is difficult to accurately assess the infant's pain based on the electroencephalogram signal. In addition to electroencephalogram signals, it is preferable to comprehensively assess infant pain based on a variety of multifaceted viewpoints. Thus, there is room for consideration of new approaches to infant pain assessment from the above perspective.

An object of the present disclosure is to provide a physiological information processing device and a physiological information processing method capable of accurately assessing infant pain based on a multifaceted perspective.

According to an aspect of the present invention, there is provided a physiological information processing device including:

one or more processors; and one or more memories for storing computer-readable commands, wherein when the computer-readable commands are executed by the processors, the physiological information processing device executes processing of:

acquiring attribute information associated with an attribution of an infant;

acquiring state information related to a state of the infant before a start of a pain event that causes pain in the infant;

acquiring physiological information data of the infant;

acquiring facial expression information associated with infant's facial expression after the start of the pain event;

calculating a pain assessment index for assessing the pain of the infant in the pain event based on the attribute information, the state information, the physiological information data, and the facial expression information; and outputting the calculated pain assessment index.

According to the above configuration, multifaceted assessment of the degree of pain of the infant during a pain event (for example, blood collection) based on the state, attribute, physiological information, and facial expression of the infant. Thus, it is possible to provide a physiological information processing device capable of accurately assessing infant pain based on a multifaceted perspective. The physiological information processing device automatically or semi-automatically acquires a pain assessment index, which greatly reduces the workload of healthcare professionals when assessing pain in the infant.

According to an another aspect of the present invention, there is provided a physiological information processing method executed by a computer, the method including:

a step of acquiring attribute information associated with an attribution of an infant;

a step of acquiring state information related to a state of the infant before a start of a pain event that causes pain in the infant;

a step of acquiring the physiological information data of the infant;

a step of acquiring facial expression information associated with infant's facial expression after the start of the pain event;

a step of calculating the pain assessment index for assessing the pain of the infant in the pain event based on the attribute information, the state information, the physiological information data, and the facial expression information; and outputting the calculated pain assessment index.

A program may be provided to cause a computer to execute the physiological information processing method. A computer readable medium may be provided in which the program is stored.

According to the present disclosure, it is possible to provide a physiological information processing device and a physiological information processing method capable of accurately assessing infant pain based on a multifaceted perspective.

BRIEF DESCRIPTION OF DRAWINGS

FIG. 5 is a flowchart for explaining the process of acquiring the facial expression information of the infant and the process of determining a pain assessment point based on the facial expression information;

FIG. 7 is a flowchart illustrating the process of determining a pain assessment point based on physiological information data;

FIG. 8 is a flowchart illustrating the process of acquiring the facial expression information of the infant according to a modification and the process of determining a pain assessment point based on the facial expression information according to the modification.

DESCRIPTION OF EMBODIMENTS

Figure 1:
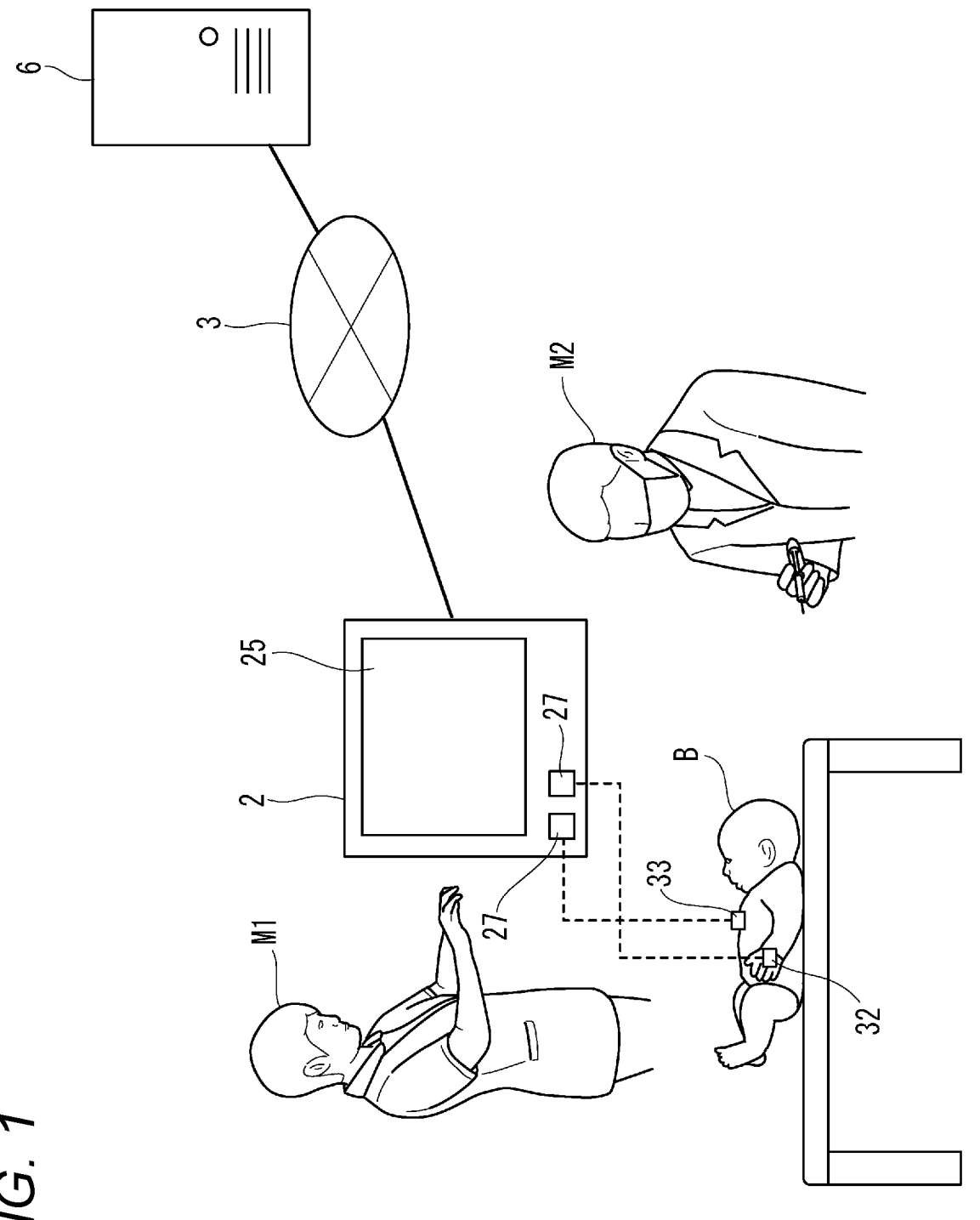
FIG. 1 is a schematic diagram illustrating a physiological information processing device according to an embodiment of the presently disclosed subject matter (hereinafter, referred to as the present embodiment)
Figure 2:
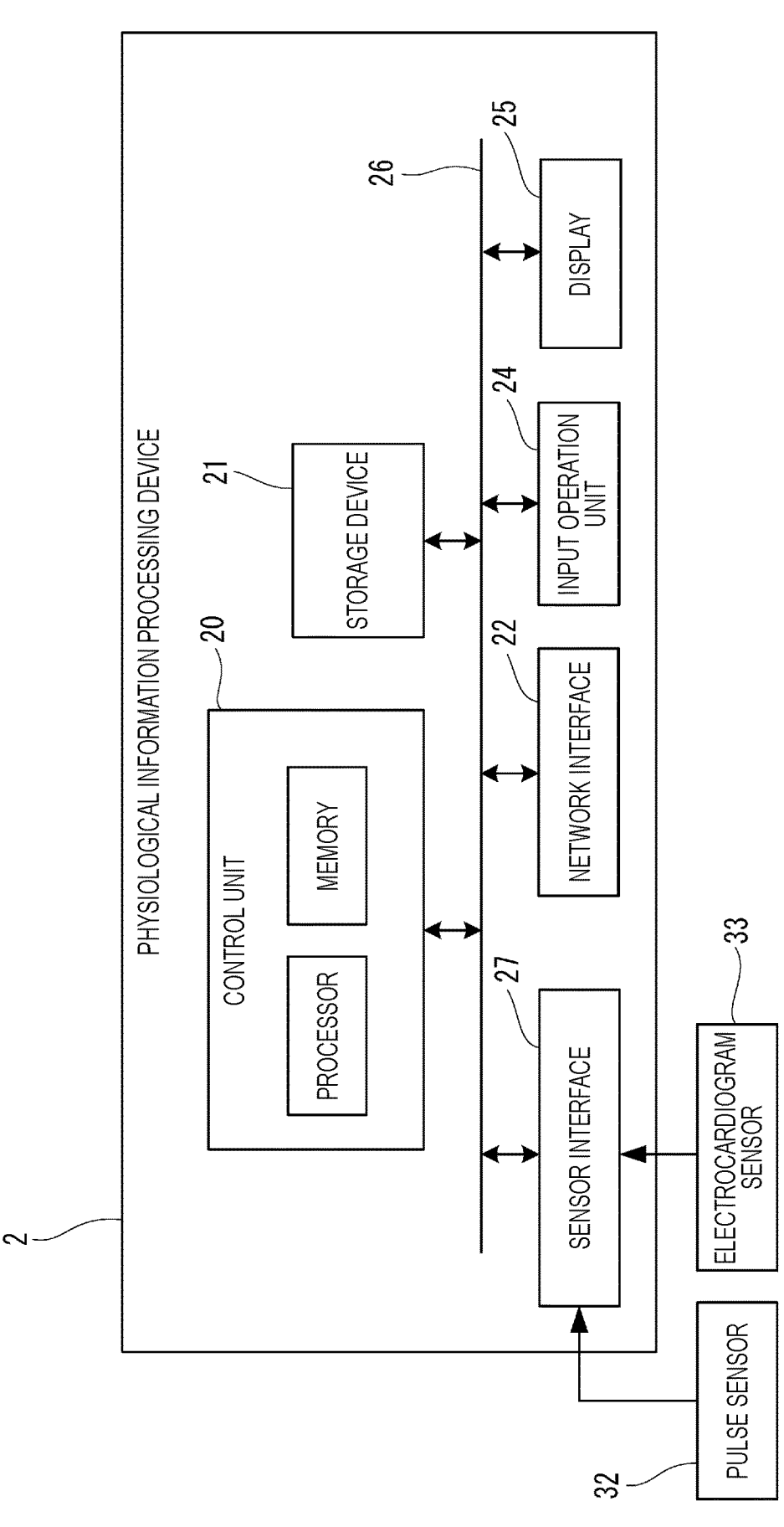
FIG. 2 illustrates an example of a hardware configuration of the physiological information processing device.

Hereinafter, a physiological information processing device 2 according to the present embodiment (hereinafter, simply the processing device 2) will be described with reference to FIGS. 1 and 2. FIG. 1 is a schematic diagram illustrating the processing device 2. FIG. 2 illustrates an example of a hardware configuration of the processing device 2.

As illustrated in FIG. 1, the processing device 2 is a device for assessing the pain of an infant B in a pain event such as blood collection. In the present embodiment, a pain assessment index for assessing the pain of the infant B is displayed on a display 25 of the processing device 2. A healthcare professional M2, who collects blood from the infant B, and a healthcare professional M1, who operates the processing device 2, can grasp the pain of the infant B during blood collection by checking the pain assessment index displayed on the display 25. The infant B is, for example, a neonate who is an infant less than 29 days old. In particular, the infant B may be a premature infant or immature infant undergoing treatment or examination in a neonatal intensive care unit (NICU). An infant with prolonged treatment after 29 days since birth may also be included. Since the infant B cannot express the degree of the pain by themselves through communication, it is necessary that the healthcare professionals M1 and M2 grasp the degree of the pain of the infant B through the processing device 2. An electrocardiogram sensor 33 and a pulse sensor 32 are attached to the infant B, and the electrocardiogram sensor 33 and the pulse sensor 32 are connected to a sensor interface 27 of the processing device 2.

As illustrated in FIG. 2, the processing device 2 includes a control unit 20, a storage device 21, a network interface 22, an input operation unit 24, a display 25, and the sensor interface 27. The units are communicatively connected to each other via a bus 26. The processing device 2 may be a specialized medical device (for example, a patient monitor, and the like) for displaying the physiological information of the infant B, or may be, for example, a personal computer, workstation, smartphone, tablet, or a wearable device worn by healthcare professionals.

The control unit 20 includes a memory and a processor. The memory is configured to store computer-readable commands (programs). For example, the memory is configured of a read only memory (ROM) storing various programs and the like, and a random access memory (RAM) having a plurality of work areas storing various programs and the like executed by the processor. The processor is configured by at least one of, for example, a central processing unit (CPU), a micro processing unit (MPU), and a graphics processing unit (GPU). The CPU may be configured by a plurality of CPU cores. The GPU may be configured by a plurality of GPU cores. The processor may be configured such that programs specified from various programs incorporated in the storage device 21 or the ROM are loaded on the RAM, and various processes are executed in cooperation with the RAM. In particular, the processor loads a physiological information processing program that executes a series of processes illustrated in FIG. 3 on the RAM, and executes the program in cooperation with the RAM, so that the control unit 20 executes the series of processes illustrated in FIG. 3. Details of the physiological information processing program will be described later.

The storage device 21 is, for example, a storage device such as a flash memory, and is configured to store programs and various data. The storage device 21 may incorporate a physiological information processing program. The storage device 21 may be stored physiological information data such as electrocardiogram data and pulse data of the infant B. For example, the pulse data acquired by the pulse sensor 32 may be stored in the storage device 21 via the sensor interface 27.

The network interface 22 is configured to connect the processing device 2 to a hospital network 3 (see FIG. 1). Specifically, the network interface 22 may include various wired connection terminals for communicating with a server 6 (see FIG. 1) via the hospital network 3. The network interface 22 may include a wireless communication module for wireless communication with the server 6. The wireless communication module may include, for example, an RF circuit and a transceiver antenna. The hospital network 3 may be configured, for example, a local area network (LAN) or a wide area network (WAN).

Figure 4:
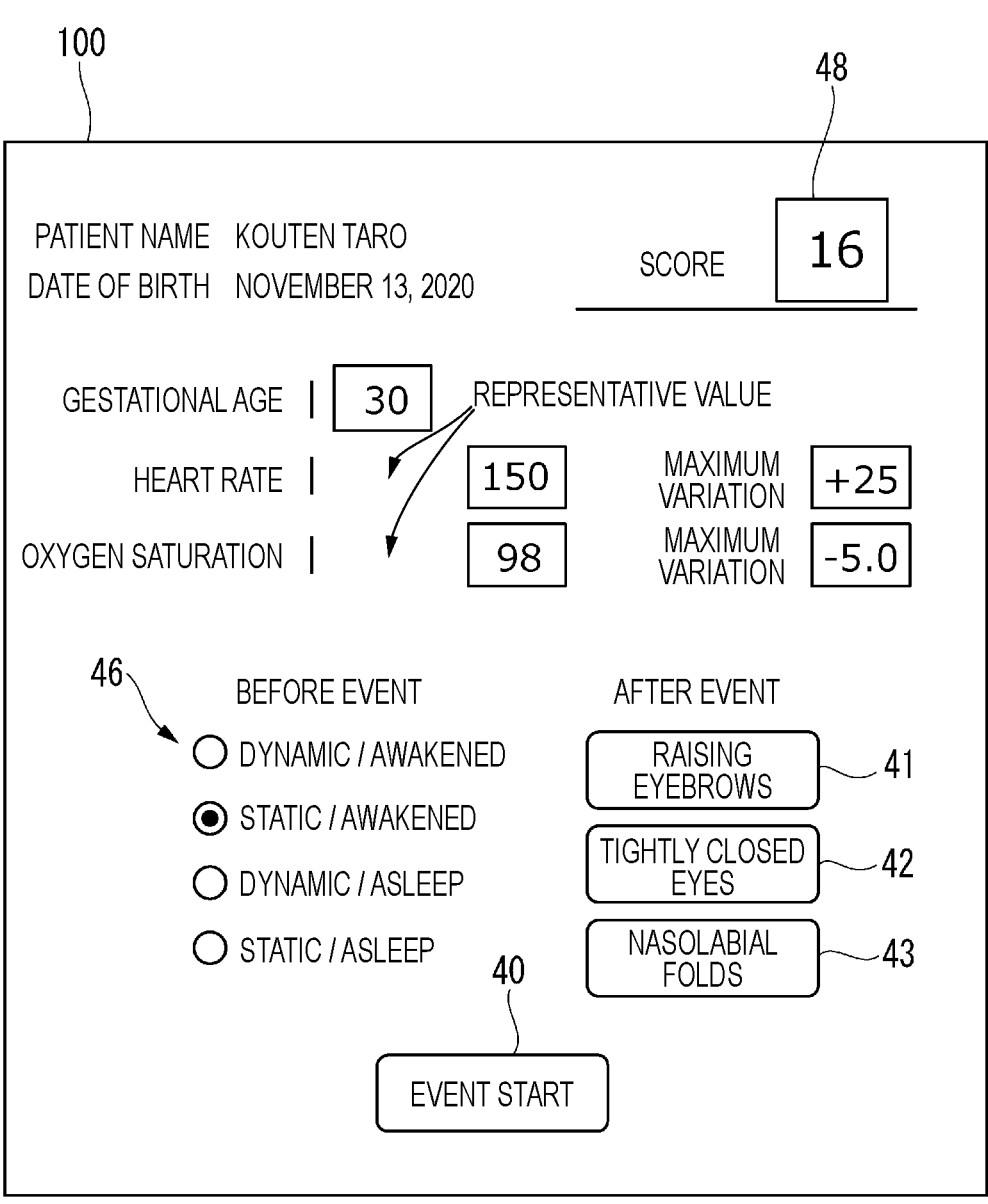
FIG. 4 illustrates an example of a GUI screen displayed on a display of the physiological information processing device.

The display 25 is configured to display the physiological information data of the infant B acquired in real time and the GUI screen 100 illustrated in FIG. 4, and is configured of, for example, a liquid crystal panel or an organic EL panel. The input operation unit 24 is configured to receive the input operation by the healthcare professional M1 and to generate an instruction signal corresponding to the input operation. The input operation unit 24 is, for example, a touch panel disposed on the display 25, a mouse, and/or a keyboard. After the instruction signal generated by the input operation unit 24 is transmitted to the control unit 20 via the bus 26, the control unit 20 executes a predetermined operation in response to the instruction signal.

The sensor interface 27 is an interface for communicatively connecting the pulse sensor 32 and the electrocardiogram sensor 33 to the processing device 2. The sensor interface 27 may include an input terminal at which physiological information data outputted from the physiological information sensors is input. The input terminals may be physically connected to the connectors of the physiological information sensors. The sensor interface 27 may also include wireless communication circuit and antennas for wireless communication with the physiological information sensors. The sensor interface 27 may also include an analog processing circuit for processing a physiological signal output from the pulse sensor 32 and the electrocardiogram sensor 33. The analog processing circuit includes, for example, a filter processing circuit for removing the noise component of the physiological signal output from the physiological information sensor, a signal amplification circuit for amplifying the physiological signal, an AD conversion circuit for converting the physiological signal from the analog signal to a digital signal. As such, the analog physiological signals output from the physiological information sensors are converted into digital physiological signals by the sensor interface 27, and then the digital physiological signals are transmitted to the control unit 20.

The electrocardiogram sensor 33 is configured to detect electrocardiogram data indicating the electrocardiogram waveform of the infant B. The pulse sensor 32 (for example, a pulse oximeter) is configured to detect pulse data indicating the pulse of the infant B. In particular, the pulse sensor 32 is configured to detect pulse data associated with red light and pulse data associated with infrared light.

Figure 3:
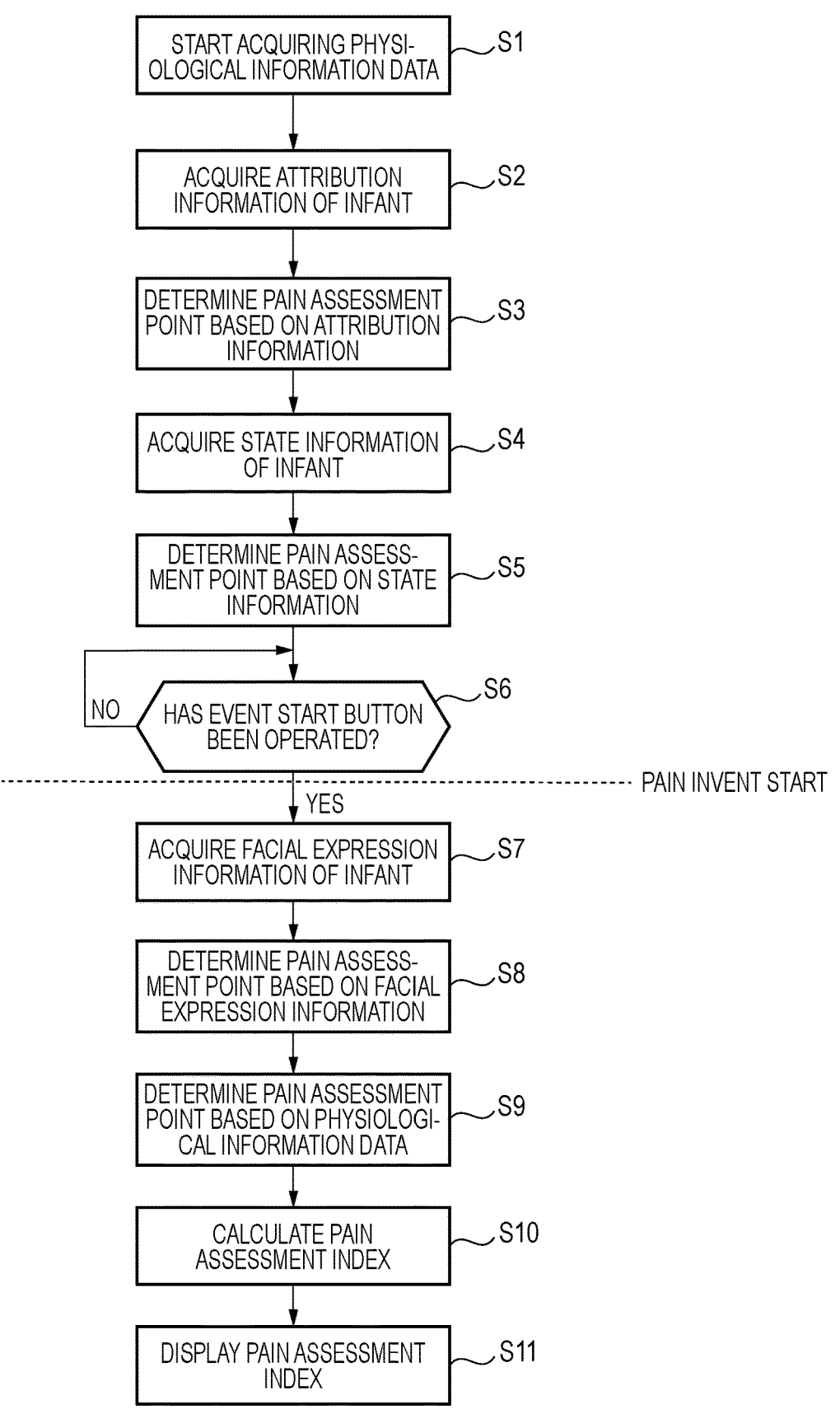
FIG. 3 is a flowchart illustrating a series of processes for determining a pain assessment index.

Next, a series of processes for determining a pain assessment index for assessing the pain of the infant B will be described below with reference to FIG. 3. FIG. 3 is a flowchart illustrating a series of processes for determining the pain assessment index. The pain assessment index calculated in the present embodiment is a pain assessment index based on premature infant pain profile (PIPP) and premature infant pain profile revised (PIPP-R). The processing device 2 according to the present embodiment is capable of automatically or semi-automatically acquiring the pain assessment index calculated based on the PIPP or PIPP-R.

As illustrated in FIG. 3, in step S1, the control unit 20 of the processing device 2 starts to acquire the physiological information data of the infant B. Specifically, the control unit 20 acquires the electrocardiogram data from the electrocardiogram sensor 33 via the sensor interface 27 and the pulse data from the pulse sensor 32 via the sense signal interface 27. Thereafter, the control unit 20 specifies the RR interval, which is the interval between adjacent QRS waveforms, based on the electrocardiogram data, and acquires the heart rate of the infant B based on the RR interval. The control unit 20 specifies the ratio of the red light intensity and the infrared light intensity based on the pulse data associated with the red light and the pulse data associated with the infrared light and acquires the percutaneous arterial blood oxygen saturation (SpO2) of the infant B based on the ratio. Note that the control unit 20 may acquire the pulse rate of the infant B based on the pulse data.

Next, in step S2, the control unit 20 acquires the attribute information of the infant B from the server 6 via the hospital network 3. In particular, the control unit 20 acquires information on the gestational age, name, and date of birth of the infant B as the attribute information of the infant B.

In step S3, the control unit 20 determines a pain assessment point based on the attribute information of the infant B. Specifically, the control unit 20 determines the pain assessment point based on the gestational age of the infant B. For example, the relationship between gestational age and pain assessment points is as follows.

TABLE 1

| Pain assessment point | 0 | 1 | 2 | 3 |
|---|---|---|---|---|
| Gestational age | 36 weeks or more | 32-35 weeks | 28-31 weeks | less than 28 weeks |

In step S4, the control unit 20 acquires the state information of the infant B. Specifically, in response to an input operation by the healthcare professional M1 to the processing device 2, the control unit 20 acquires information on the movement of the infant B (dynamic state or static state) and information on the wakefulness of the infant B (awakened state or asleep state) as the state information of the infant B. Here, as illustrated in FIG. 4, a selection area 46 is provided on the GUI screen 100 displayed on the display 25. By designating one of four options (dynamic/awakened, static/awakened, dynamic/asleep, static/asleep) displayed in the selection area 46 by the healthcare professional M1, the control unit 20 acquires the state information of the infant B. The healthcare professional M1 designates one of the four options by observing the state of the infant B with the naked eye. Note that the state information of the infant B may indicate the state of the infant B for 15 seconds immediately before the start of a pain event such as blood collection, or for 0 to 30 seconds immediately before the start of a pain event such as blood collection.

After that, the control unit 20 determines a pain assessment point based on the state information (step S5). For example, the relationship between the state information and the pain assessment points is as follows.

TABLE 2

| Pain assessment point | 0 | 1 | 2 | 3 |
|---|---|---|---|---|
| State information | dynamic/ awakened | static/ awakened | dynamic/ asleep | static/ asleep |

Next, in step S6, the control unit 20 determines whether an event start button 40 displayed on the GUI screen 100 has been operated by the healthcare professional. If the event start button 40 has been operated by the healthcare professional M1 (YES in step S6), the process proceeds to step S7. On the other hand, if the event start button 40 is not operated by the healthcare professional M1 (NO in step S6), the control unit 20 waits until the event start button 40 is operated.

Here, the healthcare professional M1 may operate the event start button 40 at the same time that a pain event such as blood collection is initiated by the healthcare professional M2. The processing device 2 recognizes the start of a pain event such as blood collection using the input operation on the event start button 40 as a trigger.

Next, in step S7, the control unit 20 acquires facial expression information related to the facial expression of the infant B according to the input operation to the processing device 2 by the healthcare professional M1. Here, the facial expression information of the infant B includes information related to the ratio of the time during which the facial expression of the infant B has a predetermined feature for a predetermined time (specifically, 30 seconds or any seconds between 0 seconds and 60 seconds) after the start of the pain event. More specifically, the facial expression information of the infant B includes information on the ratio of time during which the facial expression of the infant B has a feature related to raising the eyebrows for the predetermined time, information on the ratio of time during which the facial expression of the infant B has a feature related to closing eyes tightly for the predetermined time, and information on the ratio of time during which the facial expression of the infant B has a feature related to the nasolabial folds for the predetermined time. After that, in step S8, the control unit 20 determines the pain assessment point based on the facial expression information.

With reference to FIG. 5, the process of acquiring facial expression information of the infant (process of step S7) and the process of determining the pain evaluation point based on the facial expression information (process of step S8) will be specifically described. FIG. 5 is a flowchart illustrating the process of acquiring the facial expression information of the infant and the process of determining the pain assessment point based on the facial expression information.

As illustrated in FIG. 5, in step S20, the control unit 20 counts a first time during which the facial expression of the infant B has the feature of raising the eyebrows at the predetermined time (for 30 seconds or any seconds between 0 seconds and 60 seconds) after the start of the pain event in response to the input operation by the healthcare professional M1 to the processing device 2. Specifically, the healthcare professional M1 operates the button 41 displayed on the GUI screen 100 and the control unit 20 starts or stops counting the first time.

Figure 6:
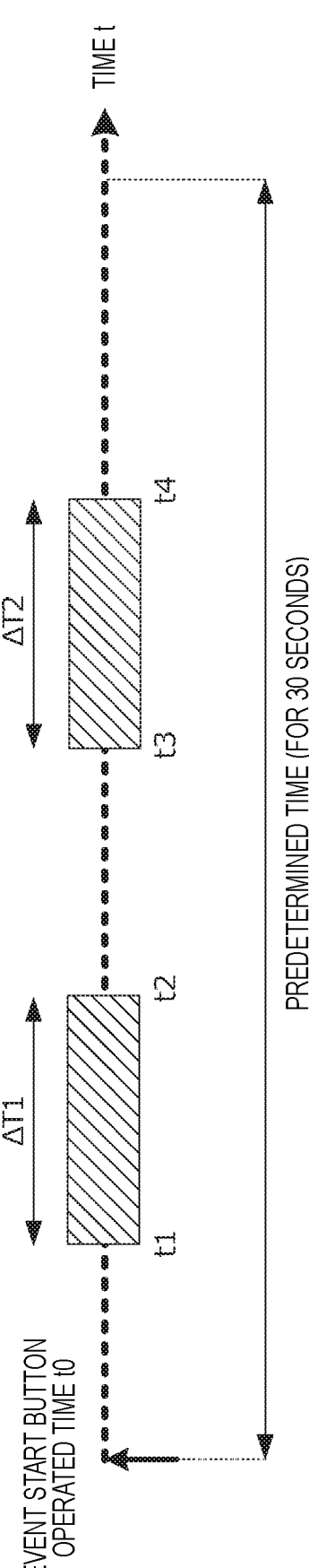
FIG. 6 is a diagram illustrating the process of counting a first time in which the facial expression of the infant has a feature of the raised eyebrows.

For example, as illustrated in FIG. 6, when the healthcare professional M1 touches the event start button 40 at time t0 and then touches the button 41 for the first time at time t1, the control unit 20 start counting the first time at time t1. After that, when the healthcare professional M1 touches the button 41 again at time t2 (in the case of the second input operation on the button 41), the control unit 20 stops counting the first time at time t2. When the healthcare professional M1 touches the button 41 at time t3 (in the case of the third input operation on the button 41), the control unit 20 restarts counting the first time at time t3. After that, when the healthcare professional M1 touches the button 41 again at time t4 (in the case of the fourth input operation on the button 41), the control unit 20 stops counting the first time at time t4. As a result, the control unit 20 counts the total time ($\Delta T1+\Delta T2$) of the time $\Delta T1$ between time t1 and time t2 and the time $\Delta T2$ between time t3 and time t4 as the first time. In this manner, through the input operation of the button 41 by the healthcare professional M1, the first time during which the facial expression of the infant B has the feature of raising the eyebrows is counted.

Note that the visual appearance of the button 41 while the first time is counting may be different from the visual appearance of the button 41 while the first time is not counting. Here, the healthcare professional M1 can intuitively grasp whether the first time is currently being counted by looking at the visual appearance of the button 41.

In step S21, the control unit 20 specifies the ratio of the first time to the predetermined time. Assuming that the predetermined time is 30 seconds, and the first time is ($\Delta T1+\Delta T2$) seconds, the ratio (%) of the first time to the predetermined time is $10(\Delta T1+\Delta T2)/3(\%)$. Next, in step S22, the control unit 20 determines the pain assessment point based on the ratio (%) of the first time to the predetermined time. For example, the relationship between the ratio of the first time and the pain assessment point is as follows.

TABLE 3

| Pain assessment point | 0 | 1 | 2 | 3 |
|---|---|---|---|---|
| Ratio of first time (%) | 0-9% | 10-39% | 40-69% | 70% or more |

In step S23, the control unit 20 counts a first time during which the facial expression of the infant B has the feature of closing eyes tightly at the predetermined time (for 30 seconds or any seconds between 0 seconds and 60 seconds) after the start of the pain event in response to the input operation by the healthcare professional M1 to the processing device 2. Specifically, the healthcare professional M1 touches the button 42 displayed on the GUI screen 100 and the control unit 20 starts or stops counting the second time. The counting method for the second time is the same as the counting method for the first time described above. The visual appearance of the button 42 while the second time is counting may be different from the visual appearance of the button 42 while the second time is not counting. In step S24, the control unit 20 specifies the ratio of the second time to the predetermined time. Next, in step S25, the control unit 20 determines the pain assessment point based on the ratio (%) of the second time to the predetermined time. The relationship between the ratio of the second time and the pain assessment point is the same as the relationship between the first time and the pain assessment point described above.

In step S26, the control unit 20 counts a third time during which the facial expression of the infant B has the feature of the nasolabial folds at the predetermined time (for 30 seconds or any seconds between 0 seconds and 60 seconds) after the start of the pain event in response to the input operation by the healthcare professional M1 to the processing device 2. Specifically, the healthcare professional M1 touches the button 43 displayed on the GUI screen 100 and the control unit 20 starts or stops counting the third time. The counting method for the third time is the same as the counting method for the first time described above. The visual appearance of the button 43 while the third time is counting may be different from the visual appearance of the button 42 while the third time is not counting. In step S27, the control unit 20 specifies the ratio of the third time to the predetermined time. Next, in step S28, the control unit 20 determines the pain assessment point based on the ratio (%) of the third time to the predetermined time. The relationship between the ratio of the third time and the pain assessment point is the same as the relationship between the first time and the pain assessment point described above.

Finally, the control unit 20 determines the pain assessment point based the facial expression by summing the pain assessment point based on the ratio of the first time associated with raising the eyebrows, the pain assessment point based on the ratio of the second time associated with closing the eyes tightly, and the pain assessment point based on the ratio of the third time associated with the nasolabial folds. As such, the control unit 20 acquires the facial expression information of the infant B and determines the pain evaluation point based on the facial expression information in response to the input operation of the buttons 41 and 42 by the healthcare professional M1. In particular, when the infant B feels pain, features related to raising the eyebrows, tightly closed eyes, and/or nasolabial folds appear in the facial expression of the infant B, thereby the pain assessment point is determined based on three features of the raised eyebrows, tightly closed eyes, and nasolabial folds.

Referring back to FIG. 3, in step S9, the control unit 20 determines the pain assessment point based on the physiological information data of the infant B. In particular, the control unit 20 determines a pain assessment point based on the heart rate of the infant B and a pain assessment point based on the oxygen saturation (SpO2) of the infant B. A series of processes for determining the pain assessment point based on physiological information data will be described below with reference to FIG. 7. FIG. 7 is a flowchart illustrating the process of determining a pain assessment point based on physiological information data.

As illustrated in FIG. 7, in step S30, the control unit 20 identifies a first representative heart rate value acquired before the start of the pain event. For example, the control unit 20 identifies the first representative value of the heart rate for 15 seconds before the time when the event start button 40 was operated by the healthcare professional M1. The first representative heart rate value may be, for example, any one of the minimum value, average value, median value, and mode value of the heart rate. Next, in step S31, the control unit 20 specifies the maximum variation of the heart rate with respect to the first representative value of the heart rate. In particular, the control unit 20 identifies the maximum variation in heart rate for the first representative value in the heart rate data acquired during a predetermined time (30 seconds or any number of seconds from 0 to 60 seconds) from the time when the event start button 40 was operated. After that, the control unit 20 determines the pain assessment point based on the maximum variation in heart rate (step S32). For example, the relationship between the maximum variation in heart rate and the pain assessment point is as follows.

TABLE 4

| Pain assessment point | 0 | 1 | 2 | 3 |
|---|---|---|---|---|
| Maximum variation of heart rate | Increase by 0-4 bpm | Increase by 5-14 bpm | Increase by 15-24 bpm | Increase by 25 bpm or more |

In step S33, the control unit 20 identifies the second representative value of the oxygen saturation acquired before the start of the pain event. For example, the control unit 20 identifies the second representative value of the oxygen saturation for 15 seconds before the time when the event start button 40 was operated by the healthcare professional M1. The second representative value of the oxygen saturation may be, for example, any one of the maximum value, average value, median value, and mode value of the oxygen saturation. Next, in step S34, the control unit 20 identifies the maximum variation in the oxygen saturation with respect to the second representative value of the oxygen saturation. In particular, the control unit 20 identifies the maximum variation in oxygen saturation for the second representative value in the oxygen saturation data acquired during a predetermined time (30 seconds or any number of seconds from 0 to 60 seconds) from the time when the event start button 40 was operated. After that, the control unit 20 determines the pain assessment point based on the maximum variation in oxygen saturation (step S35). For example, the relationship between the maximum variation in oxygen saturation and the pain assessment point is as follows.

TABLE 5

| Pain assessment point | 0 | 1 | 2 | 3 |
|---|---|---|---|---|
| Maximum variation of oxygen saturation | Reduction by 0-2.4% | Reduction by 2.5-4.9% | Reduction by 5.0-7.4% | Reduction by 7.5% or more |

The control unit 20 determines the pain assessment point based on the physiological information data by summing the pain assessment point based on the maximum variation in heart rate and the pain assessment point based on the maximum variation in oxygen saturation. Since the heart rate and oxygen saturation of the infant B change when the infant B feels pain, a pain assessment point based on the amount of change in heart rate and oxygen saturation of the infant B is determined.

In the present embodiment, the pain assessment point is determined based on the maximum variations in heart rate and oxygen saturation of the infant B, but the pain assessment point may be determined based on the maximum variations in pulse rate and oxygen saturation. Here, the control unit 20 specifies the pulse rate of the infant B based on the pulse data acquired by the pulse sensor 32. The control unit 20 specifies the representative value of the pulse rate before the start of the pain event and specifies the maximum variation in pulse rate for the representative value of the pulse rate based on the pulse rate data acquired at a predetermined time after the start of the pain event. After that, the control unit 20 determines a pain assessment point based on the maximum variation in pulse rate based on the relationship between the maximum variation in pulse rate and the pain assessment point. The relationship between the maximum variation in pulse rate and pain assessment points may be similar to the relationship between the maximum variation in heart rate and pain assessment points. When the pulse rate is employed instead of the heart rate, both the pulse rate and the oxygen saturation are acquired only by the pulse sensor 32, and thus, there is no need to attach the electrocardiogram sensor 33 to the infant B. Therefore, it is possible to assess the pain of the infant B with a simpler device configuration.

Referring back to FIG. 3, in step S10, the control unit 20 calculates the pain assessment index by summing the pain assessment point based on the attribute information, the pain assessment point based on the state information, the pain assessment points based on the physiological information data, and the pain assessment point based on the facial expression information. The pain assessment index is quantified within a range of 0 to 21 points, for example. After that, the control unit 20 displays the calculated pain assessment index on the display 25 in step S11. For example, as illustrated in FIG. 4, the pain assessment index may be displayed as numerical information within a score area 48 on the GUI screen 100. As such, the healthcare professional M2, who is performing procedures accompanying pain, such as blood collection, on the infant B, can quickly grasp the degree of pain of the infant B by looking at the pain assessment index displayed on the GUI screen 100.

According to the present embodiment, it is possible to multilaterally assess the degree of pain of the infant B in a pain event such as blood collection based on the state, attributes, physiological information, and facial expression of the infant B. Thus, it is possible to provide the processing device 2 capable of accurately assessing pain of the infant B based on a multifaceted perspective. The processing device 2 automatically or semi-automatically acquires the pain assessment index, which greatly reduces the work burden of healthcare professionals when assessing pain in the infant. Here, PIPP or PIPP-R-based pain assessment requires that healthcare professionals simultaneously acquire state information, physiological information, and facial information of the infant B while performing procedures accompanying pain on the infant B. Therefore, since pain assessment based on PIPP or PIPP-R increases the workload of healthcare professionals, pain assessment based on PIPP or PIPP-R has not been actively adopted by medical institutions. In the embodiment, the pain assessment point based on the physiological information of the infant B is automatically determined, and the workload of the healthcare professional for acquiring the facial expression information of the infant B can be greatly reduced.

In particular, since counting of the first time to the third time is started or stopped in response to the input operation by the healthcare professional to the three buttons 41 to 43 displayed on the GUI screen 100, the workload of the healthcare professional required to count the first time to the third time can be greatly reduced. Therefore, it is possible to provide the processing device 2 that greatly reduces the workload of a healthcare professional when performing pain assessment of the infant B based on PIPP or PIPP-R.

In the present embodiment, the button 41 associated with starting and stopping counting of the first time, the button 42 associated with starting and stopping counting of the second time, and the button 43 associated with starting and stopping counting of the third time are displayed on the GUI screen 100, but the present embodiment is not limited thereto. Here, each of the buttons 41 to 43 may be associated only with starting the counting of the first time to the third time. Here, another three buttons associated with stopping the counting of the first time to the third time may be displayed on the GUI screen 100.

(Modification of Processes of Steps S7 and S8)

Figure 9:
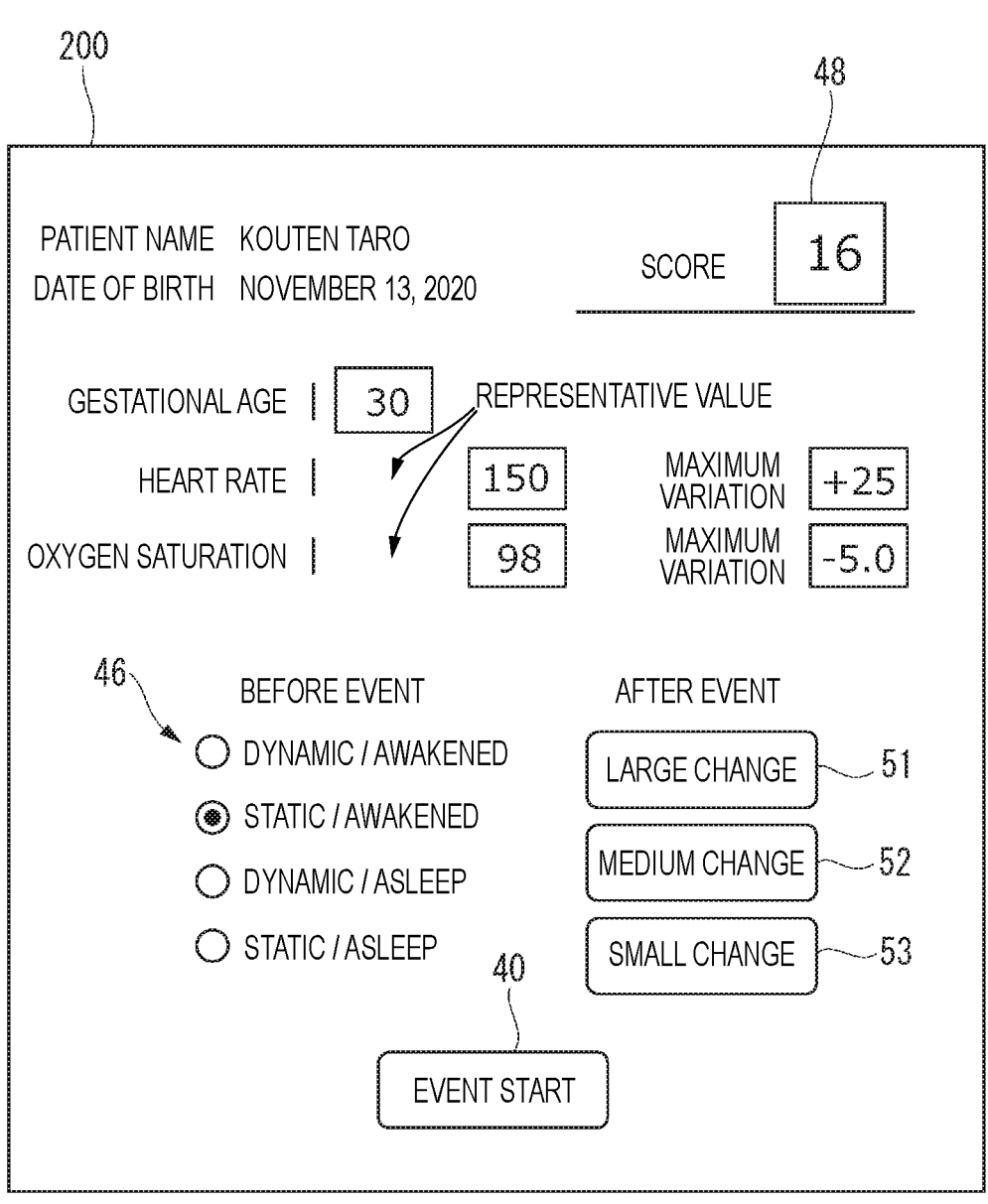
FIG. 9 illustrates another example of the GUI screen displayed on the display of the physiological information processing device.

Next, a modification of the processes of steps S7 and S8 illustrated in FIG. 3 will be described below mainly with reference to FIGS. 8 and 9. FIG. 8 is a flowchart for explaining the process of acquiring the facial expression information of the infant B according to a modification and the process of determining the pain assessment point based on the facial expression information according to the modification. FIG. 9 illustrates another example of the GUI screen displayed on the display 25 of the processing device 2. The GUI screen 200 illustrated in FIG. 9 differs from the GUI screen 100 illustrated in FIG. 4 in terms of three buttons 51 to 53 associated with facial expression information. Specifically, the button 51 is a button that is touch-operated by the healthcare professional M1 when the facial expression of the infant B changes at a large level. Specifically, the button 52 is a button that is touch-operated by the healthcare professional M1 when the facial expression of the infant B changes at a medium level. Specifically, the button 53 is a button that is touch-operated by the healthcare professional M1 when the facial expression of the infant B changes at a small level.

As illustrated in FIG. 8, in step S40, the control unit 20 counts a first time during which the facial expression of the infant B changes at a large level at the predetermined time (for 30 seconds or any seconds between 0 seconds and 60 seconds) after the start of the pain event in response to the input operation by the healthcare professional M1 to the processing device 2. Specifically, the healthcare professional M1 touches the button 41 displayed on the GUI screen 200 and the control unit 20 starts or stops counting the first time.

Now, it is assumed that the facial expression of the infant B changes at a large level if the facial expression of the infant B has all the features of the raised eyebrows, the tightly closed eyes, and the nasolabial folds. In other words, the control unit 20 counts the first time in which the facial expression of the infant B has features of the raised eyebrows, the tightly closed eyes, and the nasolabial folds are all in response to the input operation by the healthcare professional M1 to the button 51. In step S41, the control unit 20 specifies the ratio of the first time to the predetermined time. Next, in step S42, the control unit 20 determines the pain assessment point based on the ratio (%) of the first time to the predetermined time.

In step S43, the control unit 20 counts a first time during which the facial expression of the infant B changes at a medium level at the predetermined time (for 30 seconds or any seconds between 0 seconds and 60 seconds) after the start of the pain event in response to the input operation by the healthcare professional M1 to the processing device 2. Specifically, the healthcare professional M1 touches the button 41 displayed on the GUI screen 200 and the control unit 20 starts or stops counting the second time. Now, it is assumed that the facial expression of the infant B changes at a medium level if the facial expression of the infant B has two of the features of raised eyebrows, tightly closed eyes, and nasolabial folds. In other words, the control unit 20 counts the second time in which the facial expression of the infant B has features of the raised eyebrows, the tightly closed eyes, and the nasolabial folds are two features among in response to the input operation by the healthcare professional M1 to the button 52. In step S41, the control unit 20 specifies the ratio of the second time to the predetermined time. Next, in step S45, the control unit 20 determines the pain assessment point based on the ratio (%) of the second time to the predetermined time.

In step S46, the control unit 20 counts a third time during which the facial expression of the infant B changes at a small level at the predetermined time (for 30 seconds or any seconds between 0 seconds and 60 seconds) after the start of the pain event in response to the input operation by the healthcare professional M1 to the processing device 2. Specifically, the healthcare professional M1 touches the button 53 displayed on the GUI screen 200 and the control unit 20 starts or stops counting the third time. Now, it is assumed that the facial expression of the infant B changes at a small level if the facial expression of the infant B has one of the features of raised eyebrows, tightly closed eyes, and nasolabial folds. In other words, the control unit 20 counts the third time in which the facial expression of the infant B has features of the raised eyebrows, the tightly closed eyes, and the nasolabial folds are one feature among in response to the input operation by the healthcare professional M1 to the button 53. In step S47, the control unit 20 specifies the ratio of the third time to the predetermined time. Next, in step S45, the control unit 20 determines the pain assessment point based on the ratio (%) of the third time to the predetermined time.

If the facial expression of the infant B does not change at all during the predetermined period of time, the healthcare professional M1 need not operate any of the buttons 51 to 53. Here, the first time to the third time are not counted at all.

In the present modification, since counting of the first time to the third time is started or stopped in response to the input operation by the healthcare professional to the three buttons 51 to 53 displayed on the GUI screen 200, the workload of the healthcare professional required to count the first time to the third time can be greatly reduced. In the present embodiment described above, the healthcare professional M1 operates the buttons 41 to 43 displayed on the GUI screen 100 according to each feature of the raised eyebrows, tightly closed eyes, and nasolabial folds. Therefore, the workload of the healthcare professional M1 increases. For example, if the facial expression of the infant B has three features: raised eyebrows, tightly closed eyes, and nasolabial folds, the healthcare professional M1 needs to operate all buttons 41 to 43. On the other hand, in the present modification, if the infant B has three facial expressions, that is, raised eyebrows, tightly closed eyes, and nasolabial folds, the healthcare professional M1 needs only to operate the button 51.

For example, even if the facial expression having three of the raised eyebrows, tightly closed eyes, and nasolabial folds changes to the facial expression having only raised eyebrows, in the above-described embodiment, the healthcare professional M1 must operate each of the buttons 41 to 43. On the other hand, in the present modification, the healthcare professional M1 only needs to operate the button 53. As described above, in the present modification, the number of buttons to be touch-operated by the healthcare professional is reduced, so that the workload of the healthcare professional required to acquire the facial expression information is greatly reduced.

To implement the processing device 2 according to the present embodiment by software, a physiological information processing program may be preliminarily installed in the storage device 21 or ROM. Alternatively, the physiological information processing program can be stored on a magnetic disc (for example, HDD, floppy disc), optical disc (for example, CD-ROM, DVD-ROM, Blu-ray (registered trademark) disc), magneto-optical disc (for example, MO), flash memory (for example, SD card, USB memory, SSD) or other non-transitory computer-readable storage medium. Here, the physiological information processing program stored in the storage medium may be installed in the storage device 21. After the program incorporated in the storage device 21 is loaded onto the RAM, the processor may execute the program loaded onto the RAM. Thus, the processing device 2 executes a series of processes for specifying the pain assessment index illustrated in FIG. 3.

The physiological information processing program may be downloaded via the network interface 22 from a communication network. Here, the downloaded program may be installed in the storage device 21 as well.

Although the embodiments of the presently disclosed subject matter have been described above, the technical scope of the presently disclosed subject matter should not be construed to be limited by the description of the embodiments. Those skilled in the art understand that the present embodiment is merely an example, and that various modifications of the embodiment are possible within the scope of the invention described. The technical scope of the presently disclosed subject matter should be determined based on the scope of the invention described in the claims and its equivalents.

In particular, the order of processes in the flowcharts illustrated in FIG. 3 and the like is merely an example and is not particularly limited. For example, in the present embodiment, the processes of steps S3 and S5 are executed before the event start button 40 is operated, but the processes may be executed after the event start button 40 is operated.

Although the pain assessment index is displayed on the display 25 in the present embodiment, the output mode of the pain assessment index is not limited thereto. For example, the processing device 2 may audibly present information regarding the pain assessment index to the healthcare professional through a speaker. The processing device 2 may also transmit information on the pain assessment index to the server 6 through the hospital network 3. The processing device 2 may transmit information regarding the pain assessment index to a wearable device worn by the healthcare professional via near field communication.

In the present embodiment, the control unit 20 acquires the facial expression information of the infant B in response to the input operation by the healthcare professional to the processing device 2, but the present embodiment is not limited to thereto. For example, the control unit 20 may acquire the facial expression information of the infant B using an imaging device such as a camera built into the processing device 2. Here, the control unit 20 automatically acquires image data representing the face of the infant B from an imaging device, and then analyzes the image data based on an image recognition model constructed by machine learning to acquire the facial information of the baby B (that is, the first time to the third time). Here, the workload of healthcare professionals to obtain pain assessment index can be significantly reduced.

What is claimed is:

1. A physiological information processing device comprising:
   one or more processors;
   a display; and
   one or more memories for storing computer-readable commands, wherein
   when the computer-readable commands are executed by the processors, the physiological information processing device executes processing of:
   displaying on the display a button associated with a feature related to an infant's facial expressions;
   acquiring attribute information associated with an attribution of the infant;
   acquiring state information related to a state of the infant before a start of a pain event that causes pain in the infant;
   acquiring physiological information data of the infant;
   acquiring facial expression information associated with infant's facial expression after the start of the pain event based in part on input received from a user input from the button;
   identifying a first pain assessment point based on the facial expression information, wherein the facial expression information includes a ratio of a time during which the facial expression of the infant has a predetermined feature relative to a predetermined time after the start of the pain event;
   calculating a pain assessment index for assessing the pain of the infant in the pain event based on the attribute information, the state information, the physiological information data, and the facial expression information, wherein the pain assessment index comprises the first pain assessment point; and
   outputting the calculated pain assessment index.

2. The physiological information processing device according to claim 1, wherein
   the physiological information processing device executes processing of displaying the pain assessment index on the display.

3. The physiological information processing device according to claim 1, wherein
   the attribute information includes information indicating gestational age of the infant.

4. The physiological information processing device according to claim 1, wherein
   the state information includes information related to movement of the infant and information related to wakefulness of the infant.

5. The physiological information processing device according to claim 1, wherein
   the physiological information data includes data indicating a heart rate or pulse rate of the infant and data indicating oxygen saturation of the infant.

6. The physiological information processing device according to claim 5, wherein
   the physiological information processing device executes processing of:

identifying a first representative value of the heart rate or pulse rate of the infant before the start of the pain event;

identifying a second representative value of the oxygen saturation of the infant before the start of the pain event;

identifying the maximum variation in the heart rate or pulse rate of the infant with respect to the first representative value in data indicating the heart rate or pulse rate of the infant acquired during a predetermined period of time after the start of the pain event;

identifying the maximum variation in the oxygen saturation of the infant with respect to the second representative value in data indicating the oxygen saturation of the infant acquired during the predetermined time period after the start of the pain event; and calculating the pain assessment index based at least in part on the maximum variation in the heart rate or pulse rate and the maximum variation in the oxygen saturation.

7. The physiological information processing device according to claim 1, wherein the physiological information processing device executes processing of:

counting a first time during the predetermined time after the start of the pain event to determine the ratio of the first time to the predetermined time, the first time being a time during which the facial expression of the infant has a first feature;

counting a second time during the predetermined time after the start of the pain event to determine the ratio of the second time to the predetermined time, the second time being a time during which the facial expression of the infant has a second feature; and counting a third time during the predetermined time after the start of the pain event to determine the ratio of the third time to the predetermined time, the third time being a time during which the facial expression of the infant has a third feature, and the facial expression information includes information related to the ratio of the first time to the predetermined time, information related to the ratio of the second time to the predetermined time, and information related to the ratio of the third time to the predetermined time.

8. The physiological information processing device according to claim 7, wherein the first feature is a feature related to raised eyebrows, the second feature is a feature related to tightly closed eyes, and the third feature is a feature related to nasolabial folds.

9. The physiological information processing device according to claim 7, wherein the first feature is a feature having one among the raised eyebrows, the tightly closed eyes, and the nasolabial folds;

the second feature is a feature having two among the raised eyebrows, the tightly closed eyes, and the nasolabial folds; and the third feature is a feature having all of the raised eyebrows, the tightly closed eyes, and the nasolabial folds.

10. The physiological information processing device according to claim 8, wherein the physiological information processing device executes processing of:

displaying on the display a first button associated with the first feature, a second button associated with the second feature, and a third button associated with the third feature;

starting or stopping counting of the first time in response to an input operation by a healthcare professional on the first button;

starting or stopping counting of the second time in response to an input operation by the healthcare professional on the second button; and starting or stopping counting of the third time in response to an input operation by the healthcare professional on the third button.

11. The physiological information processing device according to claim 10, wherein the physiological information processing device executes processing of:

starting counting the first time in response to a first input operation by the healthcare professional on the first button;

stopping counting of the first time in response to a second input operation by the healthcare professional on the first button; and restarting counting of the first time in response to a third input operation by the healthcare professional on the first button.

12. The physiological information processing device according to claim 1, wherein the physiological information processing device executes processing of:

identifying a second pain assessment point based on the attribute information;

identifying a third pain assessment point based on the state information;

identifying a fourth pain assessment point based on the physiological information data;

calculating the pain assessment index by summing the first to fourth pain assessment points.

13. The physiological information processing device according to claim 1, wherein the physiological information processing device executes processing of:

displaying on the display an event start button associated with the start of the pain event;

receiving a first input operation by a healthcare professional on the event start button;

acquiring the attribute information and the state information before receiving the first input operation; and acquiring the facial expression information after receiving the first input operation to output the pain assessment index.

14. A physiological information processing method executed by a computer, the method comprising:

a step of displaying a button associated with a feature related to an infant's facial expressions;

a step of acquiring attribute information associated with an attribution of the infant;

a step of acquiring state information related to a state of the infant before a start of a pain event that causes pain in the infant;

a step of acquiring the physiological information data of the infant;

a step of acquiring facial expression information associated with infant's facial expression after the start of the pain event based in part on input received from a user input from the button;

a step of identifying a first pain assessment point based on the facial expression information, wherein the facial expression information includes a ratio of a time during which the facial expression of the infant has a predetermined feature relative to a predetermined time after the start of the pain event;

a step of calculating the pain assessment index for assessing the pain of the infant in the pain event based on the attribute information, the state information, the physiological information data, and the facial expression information, wherein the pain assessment index comprises the first pain assessment point; and outputting the calculated pain assessment index.

15. A non-transitory computer readable medium storing a program, the program being configured to cause a computer to execute processing of:

displaying a button associated with a feature related to an infant's facial expressions:

acquiring attribute information associated with an attribution of the infant;

acquiring state information related to a state of the infant before a start of a pain event that causes pain in the infant;

acquiring physiological information data of the infant;

acquiring facial expression information associated with infant's facial expression after the start of the pain event based in part on input received from a user input from the button;

identifying a first pain assessment point based on the facial expression information, wherein the facial expression information includes a ratio of a time during which the facial expression of the infant has a predetermined feature relative to a predetermined time after the start of the pain event;

calculating a pain assessment index for assessing the pain of the infant in the pain event based on the attribute information, the state information, the physiological information data, and the facial expression information wherein the pain assessment index comprises the first pain assessment point; and outputting the calculated pain assessment index.

* * * * *